United States Patent [19]

Phillips

[11] B 3,988,375

[45] Oct. 26, 1976

[54] PHENYL SULFONYL, BENZYLTHIOCHLOROMETHANES

[75] Inventor: Wendell Gary Phillips, Olivette, Mo.

[73] Assignee: Monsanto Company, St. Louis, Mo.

[22] Filed: May 30, 1974

[21] Appl. No.: 474,573

[44] Published under the second Trial Voluntary Protest Program on January 20, 1976 as document No. B 474,573.

Related U.S. Application Data

[62] Division of Ser. No. 399,664, Sept. 21, 1973, Pat. No. 3,839,403, which is a division of Ser. No. 139,978, May 3, 1971, Pat. No. 3,792,088.

[52] U.S. Cl. .............................. 260/609 E; 71/98; 260/465.6; 260/470; 260/481 R; 260/593 H; 260/607 A

[51] Int. Cl.² ........................................ C07C 149/34

[58] Field of Search ........ 260/609 E, 593 N, 481 R, 260/465.6, 470, 607 AR; 71/98

[56] References Cited

UNITED STATES PATENTS 3,742,066  6/1973  Tsuchihashi et al. ........... 260/609 E

OTHER PUBLICATIONS

Index of Chemicus, 30, pp. 99571 (1968).

*Primary Examiner*—Elbert L. Roberts
*Assistant Examiner*—D. R. Phillips
*Attorney, Agent, or Firm*—William I. Andress

[57] ABSTRACT

Alpha,alpha-dichloro-methane-sulfenyl chlorides and alpha-chloromethylbenzyl sulfides useful as herbicides and chemical intermediates for herbicides and their method of manufacture.

4 Claims, No Drawings

PHENYL SULFONYL, BENZYLTHIOCHLOROMETHANES

This is a division of application Ser. No. 399,664 filed Sept. 21, 1973, now U.S. Pat. No. 3,839,403, which in turn is a division of application Ser. No. 139,978, filed May 3, 1971, now U.S. Pat. No. 3,792,088.

This invention relates to substituted alpha,alpha-dichloro-methane-sulfenyl chlorides of the formula

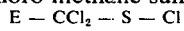

E — $CCl_2$ — S — Cl and to the intermediary alpha-chloromethylbenzyl sulfides of the formula

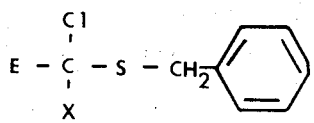

and their manufacture from the corresponding substituted methylbenzylsulfides of the formula

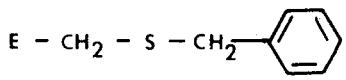

and a chlorinating agent which is sulfuryl chloride, chlorine or mixtures thereof wherein X is hydrogen or chloro, E is

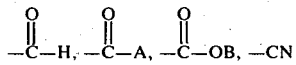

or

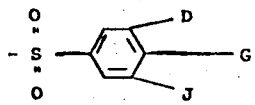

and A is aryl or halogenated aryl, B is alkyl, trihalogenated methyl or —$CH_2Y$ wherein Y is halogenated alkyl or halogenated phenyl with from one through three halogen substituents and D, G and J are hydrogen, bromo, chloro, or B as defined herein.

For A, preferred aryls include phenyl, tolyl, dimethylphenyl, ethylphenyl, cumenyl and naphthyl. More preferred are phenyl, tolyl and naphthyl. Preferred halogenated phenyls are halo-phenyl di-halo-phenyl, and tri-halo-phenyl. In more preferred halogenated phenyls the halo is fluoro, bromo, and chloro, with bromo and chloro being still more preferred.

For B, preferred alkyls include alkyls having from one through four carbon atoms and benzyl. More preferred are methyl, ethyl, propyl, isopropyl, butyl, and isobutyl. Still more preferred are methyl and ethyl.

For Y, preferred halogenated alkyls are lower alkyls having from one through four carbon atoms. By halogen is meant fluorine, chlorine, bromine and iodine. More preferred halogenated alkyls include methyl, ethyl, propyl, isopropyl, butyl, and isobutyl. Still more preferred halogenated alkyls are methyl having from one through three bromine or chlorine atoms. When Y is halogenated phenyl it is likewise preferred that the halogen be bromine or chlorine.

Examples of substituted alpha,alpha-dichloro-methane-sulfenyl chlorides include, but are not limited to:
alpha,alpha-dichloro-alpha-(chloromercapto)-acetonitrile,
alpha,alpha-dichloro-alpha-(chloromercapto)-acetaldehyde,
alpha,alpha-dichloro-alpha-(4-chlorobenzoyl)-methane-sulfenyl chloride,
alpha,alpha-dichloro-alpha-(2-chlorobenzyl)-methane-sulfenyl chloride,
alpha,alpha-dichloro-alpha-(4-bromobenzoyl)-methane-sulfenyl chloride,
alpha,alpha-dichloro-alpha-(3-fluorobenzoyl)-methane-sulfenyl chloride,
alpha,alpha-dichloro-alpha-(benzoyl)-methane-sulfenyl chloride,
alpha,alpha-dichloro-alpha-(2,6-dichlorobenzoyl)-methane-sulfenyl chloride,
alpha,alpha-dichloro-alpha-(3,4,5-trichlorobenzoyl)-methane-sulfenyl chloride,
alpha,alpha-dichloro-alpha-(2,4,6-tribromobenzoyl)-methane-sulfenyl chloride,
alpha,alpha-dichloro-alpha(4-methylbenzoyl)-methane-sulfenyl chloride,
alpha,alpha-dichloro-alpha-(2-methylbenzoyl)-methane-sulfenyl chloride,
alpha,alpha-dichloro-alpha-(4-ethylbenzoyl)-methane-sulfenyl chloride,
alpha,alpha-dichloro-alpha-(3-methylbenzoyl)-methane-sulfenyl chloride,
alpha,alpha-dichloro-alpha-naphthoyl-methane-sulfenyl chloride,
alpha,alpha-dichloro-alpha-(4-propylbenzoyl)-methane-sulfenyl chloride,
methyl alpha-(chloromercapto)-alpha,alpha-dichloroacetate,
propyl alpha-(chloromercapto)-alpha,alpha-dichloroacetate,
isopropyl alpha-(chloromercapto)-alpha,alpha-dichloroacetate, butyl alpha-(chloromercapto)-alpha,alpha-dichloroacetate,
isobutyl alpha-(chloromercapto)-alpha,alpha-dichloroacetate,
benzyl alpha-(chloromercapto)-alpha,alpha-dichloroacetate,
beta-chloroethyl alpha-(chloromercapto)-alpha,alpha-dichloroacetate,
beta-bromopropyl alpha-(chloromercapto)-alpha,alpha-dichloroacetate,
gamma-chloropropyl alpha-(chloromercapto)-alpha,alpha-dichloroacetate,
para-chlorobenzyl alpha-(chloromercapto)-alpha,alpha-dichloroacetate,
para-bromobenzyl alpha-(chloromercapto)-alpha,alpha-dichloroacetate,
para-fluorobenzyl alpha-(chloromercapto)-alpha,alpha-dichloroacetate,
beta,beta-dichloroethyl alpha-(chloromercapto)-alpha,alpha-dichloroacetate,
ethyl alpha-(chloromercapto)-alpha,alpha-dichloroacetate,
2,4-dichlorobenzyl alpha-(chloromercapto)-alpha,alpha-dichloroacetate,
3,4-dichlorobenzyl alpha-(chloromercapto)-alpha,alpha-dichloroacetate, trichloromethyl alpha-(chloromercapto)-alpha,alpha-dichloroacetate,
2,3,4-trichlorobenzyl alpha-(chloromercapto)-alpha,alpha-dichloroacetate,
alpha-phenylsulfonyl-alpha,alpha-dichloro-methane-sulfenyl In the overall manufacture of alpha,alpha-dichloromethane-sulfenyl chlorides of this invention from substituted methyl-benzyl sulfides a stepwise reaction occurs which, while not completely understood in the matter of its mechanism, can be represented by the following chemical equations wherein X is benzyl

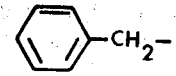

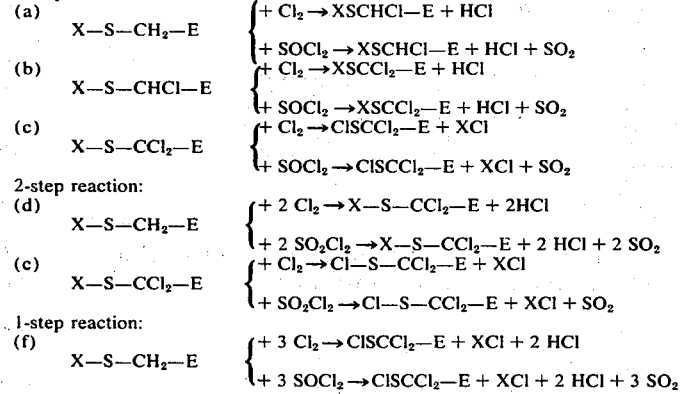

alpha-(meta-chlorophenylsulfonyl)-alpha,alpha-dichloromethane-sulfenyl chloride,
alpha-(para-chlorophenylsulfonyl)-alpha,alpha-dichloromethane-sulfenyl chloride,
alpha-(3,4-dichlorophenylsulfonyl)-alpha,alpha-dichloromethane-sulfenyl chloride,
alpha-(3,5-dichlorophenylsulfonyl)-alpha,alpha-dichloromethane-sulfenyl chloride,
alpha-(para-bromophenylsulfonyl)-alpha,alpha-dichloro-methane-sulfenyl chloride,
alpha-(3-chloro-4-bromophenylsulfonyl)-alpha,alpha-dichloromethane-sulfenyl chloride,
alpha-(3,4-dibromophenylsulfonyl)-alpha,alpha-dichloro-methane-sulfenyl chloride,
alpha-(3,4,5-trichlorophenylsulfonyl)-alpha,alpha-dichloromethane-sulfenyl chloride,
alpha-(3,5-dichloro-4-bromophenylsulfonyl)-alpha,alpha-dichloro-methane-sulfenyl chloride,
alpha-(3-methylphenylsulfonyl)-alpha,alpha-dichloro-methane-sulfenyl chloride,
alpha-(4-methylphenylsulfonyl)-alpha,alpha-dichloro-methane-sulfenyl chloride,
alpha-(3,4-dimethylphenylsulfonyl)-alpha,alpha-dichloromethane-sulfenyl chloride,
alpha-(3,5-dimethylphenylsulfonyl)-alpha,alpha-dichloro-methane-sulfenyl chloride,
alpha-(4-ethylphenylsulfonyl)-alpha,alpha-dichloromethane-sulfenyl chloride,
alpha-(3-chloromethylphenylsulfonyl)-alpha,alpha-dichloromethane-sulfenyl chloride,
alpha-(3,4-diethylphenylsulfonyl)-alpha,alpha-dichloromethane-sulfenyl chloride,
alpha-(3,4,5-trimethylphenylsulfonyl)-alpha,alpha-dichloromethane-sulfenyl chloride,
alpha-(3,5-dichloro-4-methylphenylsulfonyl)-alpha,alpha-dichloro-methane-sulfenyl chloride,
alpha-(3,4,5-tribromophenylsulfonyl)-alpha,alpha-dichloromethane-sulfenyl chloride,
and the like. These compounds are soluble in most common organic solvents but are insoluble in water.

From the foregoing equations, it is clear that the reaction of this invention may be conducted in one, two or three steps by control of the concentration of the chlorinating agent. The chlorinating agent may be chlorine alone, sulfuryl chloride alone, or a mixture of any proportion of chlorine and sulfuryl chloride. When the alpha,alpha-dichloro-alpha-chloromercapto product is the desired reaction product, the chlorinating agent may be present in excess and the reaction may be carried out at any temperature from above the freezing point of the system to about the boiling point of the system at the desired pressure under which the reaction is conducted.

Since gaseous reaction products are evolved, the reaction is usually carried out at atmospheric pressure but higher or lower pressures may be utilized if equipment and other factors favor such higher or lower pressures. The reaction may be carried out in an open vessel or under reflux.

It is preferable to conduct the reaction in the presence of an inert organic liquid, but when reaction conditions are mild, i.e., the reaction is conducted at a temperature below about 30°C., an excess of sulfuryl chloride may perform the solvating function of the inert organic liquid and there is no necessity for the inert liquid in the reaction system. In a preferred embodiment of the process for the preparation of alpha,alpha-dichloro-methane-sulfenyl chlorides in the presence of an inert organic liquid, there will be employed for each mole of precursor substituted methylbenzyl sulfide from 3 to 6 moles of chlorine or sulfuryl chloride or mixture thereof. The reaction is preferably carried out at a temperature above the freezing point of the system but below the boiling of the inert organic liquid. More preferably the reaction is carried out at temperatures of from about 0°C. to about 100°C. and still more preferably from about 0° to about 30°C.

The intermediary alpha-chloromethylbenzyl sulfide and alpha,alpha-dichloromethylbenzyl sulfide are obtained by mixing in an inert organic liquid to effect evolution of hydrogen chloride, depending on which of the two intermediate products is desired, one molecular proportion of precursor substituted methylbenzyl sulfide and about one or about two molecular proportions of chlorine or sulfuryl chloride (when sulfuryl chloride is employed instead of chlorine in whole or in part sulfur dioxide also evolves as a by-product along with by-product hydrogen chloride) at a temperature above the freezing point of the system. Whichever of said intermediary products is desired to be produced, it is readily isolated from this reaction mass, as for example by evaporation of the inert organic liquid and recrystallization of the residue in the cold to give the intermediate product. The yield of the said intermediary is generally one hundred percent, but declines as the reaction temperature increases above the range of from about 25°C. to about 30°C., the formation of benzyl chloride being observed. Since the chlorination appears to proceed in a stepwise fashion, intermediary products may likewise be obtained even when the chlorinating agent is present in quantities greater than the stoichiometric amount for the desired product so long as reaction conditions are very mild; i.e., the temperature is maintained below 20° Centigrade and reaction time does not exceed about 1 hour.

Precursor substituted methylbenzyl sulfides are readily obtainable by initially slowly mixing at about room temperature one molecular proportion of a substituted chloromethane (Cl—CH$_2$—E) corresponding to the desired substituted methylbenzyl sulfide with an aqueous solution containing one molecular proportion of benzyl mercaptan and one molecular proportion of sodium hydroxide, thereafter refluxing the so-charged mass for about 12 hours, cooling to about room temperature, extracting the cooled mass with methylene chloride, and then separating the product by evaporating methylene chloride from the extract, and if necessary vacuum distilling the product to purify same.

The inert organic liquid employed in the overall manufacture of this invention or any portion thereof can be any organic liquid, or mixtures thereof, which is inert under the reaction conditions, and preferably having a boiling point in the range of from about 30°C. to about 100°C. Ordinarily, the inert organic liquid comprises liquid alkanes or liquid chloroalkanes or various mixtures thereof, for example; pentane, 3-ethylpentane, hexane, 2-ethylhexane, heptane, dichloromethane, 1,1-dichloroethane, chloroform, carbon tetrachloride, isobutyl chloride, and various mixtures thereof. In general it is preferable but not necessary that the amount of said inert organic liquid present throughout the course of the reaction be that at least sufficient to maintain the intermediary alpha-chloromethylbenzyl sulfide in solution. Where the reactions are carried out in step-wise fashion in proceeding from a precursor through intermediary alpha-chloromethylbenzyl sulfides to an alpha,alphadichloro-alpha-(chloromercapto) compound, the inert organic liquid will usually be the same as that employed in preparing the intermediate or intermediaries; however, such can be replenished or replaced in whole or in part by a different inert organic liquid in any or each step.

In the matter of pressure, either that above or below atmospheric pressure can be employed, however, in general atmospheric pressure will be satisfactory.

Substituted alpha,alpha-dichloro-methane-sulfenyl chlorides exhibit herbicidal activity toward noxious weeds and have particular utility as selective pre-emergent herbicides.

As illustrative of this invention but not limitative thereof is the following:

EXAMPLES 1 THROUGH 5

These examples illustrate the preparation by the method of this invention of alpha,alpha-dichloromethane-sulfenyl chlorides of the formula E—CCl$_2$—S—Cl and intermediary alpha-chloromethylbenzyl sulfides of the formula

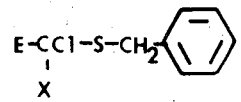

wherein X is hydrogen or chloro and E is —CN.

EXAMPLE 1

Precursor alpha-(benzylmercapto)acetonitrile is an oily substance readily obtainable by initially slowly mixing at about room temperature one molecular proportion of chloroacetonitrile (Cl—CH$_2$—CN) with an aqueous solution containing one molecular proportion of benzyl mercaptan and one molecular proportion of sodium hydroxide, thereafter refluxing the so-charged mass for about 12 hours, cooling to about room temperature, extracting the cooled mass with methylene chloride, and then separating the oily product by evaporating methylene chloride from the extract, and if necessary vacuum distilling the oily product to purify same.

EXAMPLE 2

To a suitable reaction vessel equipped with an agitator, thermometer and means for venting by-product hydrogen chloride and sulfur dioxide is charged 16.3 parts by weight (substantially 0.10 mole) of alpha-(benzylmercapto)-acetonitrile in 100 parts by weight of methylene chloride. While maintaining the so-charged solution at about 0°C. there is added with agitation 40 parts by weight (substantially 0.30 mole) of sulfuryl chloride. Upon completion of this addition the mass is permitted to warm to room temperature and then maintained at about room temperature for 1 hour while constantly agitating the mass. Thereupon the methylene chloride, and residual volatiles if any, are evaporated under vacuum. The residue is admixed with petroleum ether and cooled employing dry ice. A solid precipitate is filtered off, which solid, an off-white color, liquefies to a yellow liquid at room temperature and is identified as alpha, alpha-dichloro-alpha-(benzylmercapto)-acetonitrile. The yield is approximately 100%.

Alpha,alpha-dichloro-alpha-(benzylmercapto)-acetonitrile exhibited pre-emergent herbicidal activity against cocklebur, velvet leaf, smartweed and barnyard grass, *Eichinochloa crusgali.*

Additionally, alpha,alpha-dichloro-alpha-(benzylmercapto)acetonitrile shows contact herbicidal activity, for example applying as an aqueous spray at a concentration of 0.2 percent by weight at a rate of 4 pounds of said intermediary per acre to plots having 14 day established growths of barnyard grass, *Eichinochloa crusgali,* and inspecting the so-treated plots 14 days after said application under ordinary conditions of sunlight and watering revealed severe phytotoxicity to said barnyard grass species.

EXAMPLE 3

The alpha,alpha-dichloro-alpha-(benzylmercapto)-acetonitrile isolated product of Example 2 is dissolved in 1,2-dichloroethane and heated to the reflux temperature which is about 84° Centigrade. Thereupon chlorine is sparged into the refluxing mass over a period of about 1 hour, in which time approximately one molar equivalent is absorbed. The reaction mass is cooled and subjected to fractional distillation to separate alpha-alphadichloro-alpha-(chloromercapto)-acetonitrile from by-product benzyl chloride.

EXAMPLE 4

To a suitable reaction vessel equipped with an agitator, thermometer and means for venting by-product hydrogen chloride and sulfur dioxide is charged 16.3 parts by weight (substantially 0.10 mole) of alpha-(benzylmercapto)-acetonitrile in 100 parts by weight of methylene chloride. While maintaining the so charged solution at about 0°C. there is added with agitation 40 parts by weight (substantially 0.30 mole) of sulfuryl chloride. Upon completion of this addition the mass is permitted to warm to room temperature and then maintained at about room temperature for 1 hour while constantly agitating the mass. Thereupon chlorine gas is bubbled through the agitated mass while permitting the temperature to rise to the reflux temperature (about 41°C.) and then refluxed for about one hour. The amount of chlorine absorbed amounts to about 7.1 parts by weight (substantially 0.1 mole). The mass is cooled and subjected to fractional distillation yielding alpha,alpha-dichloro-alpha-(chloromercapto)-acetonitrile at 65°–66°C. at 30 mm of mercury.

EXAMPLE 5

To a suitable reaction vessel equipped with an agitator, thermometer and means for venting by-product hydrogen chloride and sulfur dioxide is charged 16.3 parts by weight (substantially 0.10 mole) of alpha-(benzylmercapto)-acetonitrile in 100 parts by weight of methylene chloride. While maintaining the so-charged solution at about 0°C. there is added with agitation 53.6 parts by weight (substantially 0.40 mole) of sulfuryl chloride. Upon completion of this addition the mass is permitted to warm to room temperature and then maintained at about room temperature for one hour while constantly agitating the mass. Thereupon the methylene chloride solution containing alpha,alpha-dichloro-alpha-(benzylmercapto)-acetonitrile and residual sulfuryl chloride is refluxed (about 41°C) for 15 minutes and thereafter cooled and subjected to a spinning band fractional distillation to give alpha,alphadichloro-alpha-(chloromercapto)-acetonitrile.

Alpha,alpha-dichloro-alpha-(chloromercapto)-acetonitrile exhibited pre-emergent herbicidal activity against cocklebur, morning glory and lambsquarter species and insecticidal activity against southern corn root worm.

EXAMPLES 6 THROUGH 36

These examples illustrate the preparation by the method of this invention of alpha,alpha-dichloromethane-sulfenyl chlorides of the formula E-CCl$_2$-S-Cl and intermediary alpha-chloromethylbenzyl sulfides of the formula

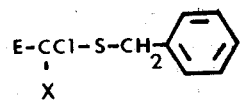

wherein X is hydrogen or chloro and E is

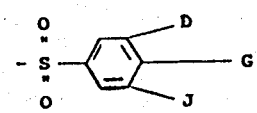

and D, G and J are hydrogen, bromo, chloro, alkyl, or B as defined in this specification.

EXAMPLE 6

To a suitable reaction vessel equipped with a thermometer, agitator and reflux condenser is charged approximately 10.3 parts by weight of benzyl mercaptan and approximately 48 parts by weight of dimethylformamide having dissolved therein approximately 2.0 parts by weight of sodium hydride. Thereupon and while agitating is added approximately 95 parts by weight of dimethylformamide having dissolved therein approximately 15.7 parts by weight of alpha-(phenylsulfonyl)-methyl chloride.

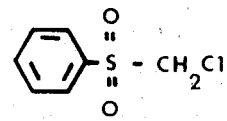

The mass is then heated to the reflux temperature and refluxed for about 16 hours. The mass is cooled to room temperature and admixed with approximately 250 parts by weight of cold water, and thereafter extracted initially with diethylether and finally with methylene chloride. The extracts are combined and the resultant solution evaporated. The residual slurry is admixed with diethylether and filtered. The precipitate, a white solid (m.p. 105°–107°C.), is alpha-(benzylmercapto)-methyl phenylsulfone

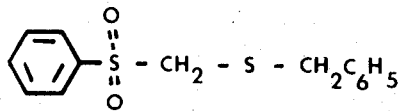

Alpha-(benzylmercapto)-methyl phenyl sulfone exhibited preemergent herbicidal activity against morning glory, smartweed and nutsedge.

EXAMPLE 7

Employing the procedure of Example 6 but replacing alpha-(phenylsulfonyl)-methyl chloride with an equimolecular amount of alpha-(4-chlorophenylsulfonyl)-methyl chloride there is obtained alpha-(benzylmercapto)-methyl para-chlorophenylsulfone

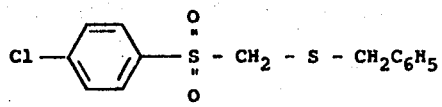

EXAMPLE 8

Employing the procedure of Example 6 but replacing alpha-(phenylsulfonyl)-methyl chloride with an equimolecular amount of alpha-(3,4-dichlorophenylsulfonyl)-methyl chloride there is obtained alpha-(benzylmercapto)-methyl 3,4-dichlorophenylsulfone

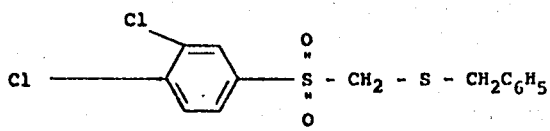

Similarly alpha-(benzylmercapto)-methyl 3,4,5-trichlorophenylsulfone, alpha-(benzylmercapto)-methyl 3-bromo-4-chlorophenylsulfone and alpha-(benzylmercapto)-methyl 4-bromo-3,5-dichlorophenylsulfone are prepared employing respectively alpha-(3,4,5-trichlorophenylsulfonyl)-methyl chloride, alpha-(3-bromo-4-chlorophenylsulfonyl)-methyl chloride and alpha-(4-bromo-3,5-dichlorophenylsulfonyl)-methyl chloride. Additionally, other alpha-(benzylmercapto)-substituted phenylsulfones can be prepared from the corresponding substituted phenylsulfonylmethyl chlorides.

EXAMPLE 9

To a suitable reaction vessel equipped with a thermometer and agitator and means for venting by-product hydrogen chloride is charged in the cold approximately 7.0 parts by weight of alpha(benzylmercapto)-methyl phenylsulfone dissolved in approximately 138 parts by weight of methylene chloride. While maintaining the temperature of the so charged mass at about 0°C. approximately 10.1 parts by weight of sulfuryl chloride is slowly added. Thereafter the mass is permitted to rise to about 20°C. over a period of about 1 hour with constant agitation. The volatiles, principally methylene chloride, are evaporated at room temperature to give an oil which upon taking up with diethyl ether and cooling yields white solid (m.p. 83.5°–84.5°C.)alpha-(benzylmercapto)-alpha, alpha-dichloromethyl phenylsulfone

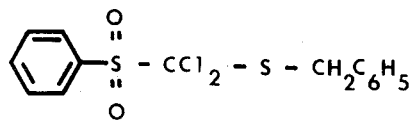

Alpha-(benzylmercapto)-alpha,alpha-dichloromethyl phenylsulfone exhibited preemergent herbicidal activity against lambsquarter, smartweed, nutsedge and Johnson grass.

EXAMPLE 10

Employing the procedure of Example 9 but replacing alpha(benzylmercapto)-methyl phenylsulfone with an equimolecular amount of alpha-(benzylmercapto)-methyl para-chlorophenylsulfone there is obtained alpha-(benzylmercapto)-alpha,alpha-dichloromethyl parachlorophenylsulfone

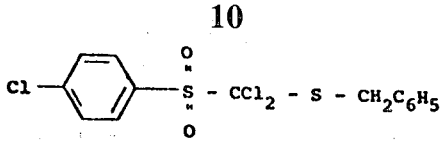

EXAMPLE 11

Employing the procedure of Example 9 but replacing alpha-(benzylmercapto)-methyl phenylsulfone with an equimolecular amount of alpha-(benzylmercapto)-methyl 3,4-dichlorophenylsulfone there is obtained alpha-(benzylmercapto)-alpha,alpha-dichloromethyl 3,4-dichlorophenylsulfone

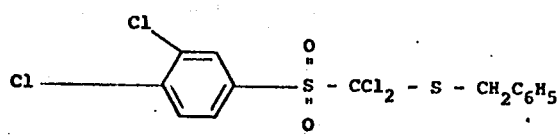

EXAMPLE 12

Employing the procedure of Example 9 but instead of charging sulfuryl chloride bubbling through the charged mass chlorine, while maintaining the temperature at about 0°C. until approximately 3.6 parts by weight of chlorine is absorbed, there is obtained, employing the same recovery procedure as in Example 9, white solid alpha-(benzylmercapto)-alpha,alpha-dichloromethyl phenylsulfone.

In like manner alpha-(benzylmercapto)-alpha,alpha-dichloromethyl 3,4,5-trichlorophenylsulfone, alpha-(benzylmercapto)-alpha,alpha-dichloromethyl 3-bromo-4-chlorophenylsulfone, and alpha-(benzylmercapto)-alpha,alpha-dichloromethyl 4-bromo-3,5-dichlorophenyl-sulfone are prepared employing the appropriate alpha-(benzylmercapto)-methyl substituted-phenylsulfone. This same method may be used to prepare other alpha-chloro-alpha-(benzylmercapto)-substituted phenylsulfones, from the corresponding precursor.

EXAMPLE 13

To a suitable reaction vessel equipped with a thermometer, agitator and reflux condenser is charged approximately 34.8 parts by weight of alpha-(benzylmercapto)-alpha,alpha-dichloromethyl phenylsulfone and approximately 27.1 parts by weight of sulfuryl chloride and the so charged mass heated to the reflux temperature and refluxed for about 2 hours. The residue is then evaporated to give an oil which is taken up with petroleum ether, cooled and the precipitate filtered off. The filter cake is white solid (m.p. 62°–64°C.) alpha-(phenylsulfonyl)-alpha,alpha-dichloromethanesulfenyl chloride

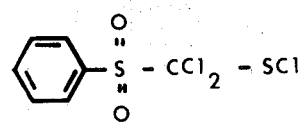

EXAMPLE 14

To a suitable reaction vessel equipped with a thermometer, agitator and reflux condenser is charged approximately 35.0 parts by weight of alpha-(benzylmercapto)-alpha,alpha-dichloromethyl para-chlorophenylsulfone and approximately 600 parts by weight of 1,2-dichloroethane and the so-charged mass heated to the reflux temperature. While refluxing chlorine is sparged into the refluxing mass until approximately 7.0 parts by weight thereof are absorbed. The reaction mass is then evaporated to remove the volatiles, principally 1,2-dichloromethane, to give a residue which upon taking up with petroleum ether and cooling precipitates alpha-(para-chlorophenylsulfonyl)-alpha,alpha-dichloro-methane-sulfenyl chloride

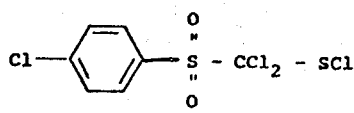

EXAMPLE 15

To a suitable reaction vessel equipped with an agitator, thermometer and reflux condenser is charged approximately 37.3 parts by weight of alpha-(benzylmercapto)-alpha,alpha-dichloromethyl 3,4-dichlorophenylsulfone and approximately 42 parts by weight of sulfuryl chloride and the so-charged mass heated to the reflux temperature and refluxed for about 2 hours. The residue is evaporated to rid it of volatiles and then taken up with petroleum ether, cooled and the precipitate filtered off to give alpha-(3,4-dichlorophenylsulfonyl)-alpha,alpha-dichloro-methane-sulfenyl chloride

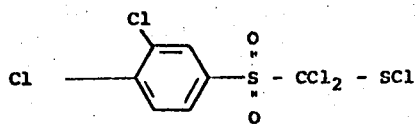

EXAMPLE 16

To a suitable reaction vessel equipped with a thermometer and agitator and means for venting by-product hydrogen chloride is charged in the cold approximately 7.0 parts by weight of alpha-(benzylmercapto)-methyl phenylsulfone dissolved in approximately 138 parts by weight of methylene chloride. While maintaining the temperature of the so charged mass at about 0°C. approximately 10 parts by weight of sulfuryl chloride is slowly added. Thereafter the so charged mass is heated to the reflux temperature and refluxed for about two hours. The residue is then evaporated to give an oil which is taken up with petroleum ether, cooled and the precipitate filtered off. The filter cake is white solid (m.p. 62°–64°C.) alpha-(phenylsulfonyl)-alpha,alpha-dichloro-methane-sulfenyl chloride

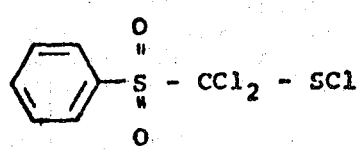

EXAMPLE 17

Employing the procedure of Example 16 but instead of charging sulfuryl chloride bubbling through the charged mass, chlorine while maintaining the temperature at reflux temperature until approximately 6 parts by weight of chlorine is absorbed, there is obtained, employing the same recovery procedure as in Example 15, white solid alpha-(phenylsulfonyl)-alpha,alpha-dichloro-methane-sulfenyl chloride.

Alpha-(phenylsulfonyl)-alpha,alpha-dichloro-methane sulfenyl chloride exhibited preemergent herbicidal activity against velvet leaf, lambsquarter, smartweed and quackgrass.

EXAMPLES 18 THROUGH 36

Employing the procedure of Example 16 but replacing alpha-(benzylmercapto)-methyl phenylsulfone with an equimolecular amount of alpha-(benzylmercapto)-substituted phenylsulfone of Column A there is obtained the corresponding alpha-(phenylsulfonyl)-alpha,alpha-dichloro-methane-sulfenyl chloride of Column B.

| EXAMPLE | COLUMN A | COLUMN B |
| --- | --- | --- |
| 18 | alpha-(benzylmercapto)-methyl meta-chlorophenylsulfone | alpha-(meta-chlorophenylsulfonyl)-alpha,alpha-dichloro-methane-sulfenyl chloride |
| 19 | alpha-(benzylmercapto)-methyl para-chlorophenylsulfone | alpha-(para-chlorophenylsulfonyl)-alpha,alpha-dichloro-methane-sulfenyl chloride |
| 20 | alpha-(benzylmercapto)-methyl 3,4-dichlorophenylsulfone | alpha-(3,4-dichlorophenylsulfonyl)-alpha,alpha-dichloro-methane-sulfenyl chloride |
| 21 | alpha-(benzylmercapto)-methyl 3,5-dichlorophenylsulfone | alpha-(3,5-dichlorophenylsulfonyl)-alpha,alpha-dichloro-methane-sulfenyl chloride |
| 22 | alpha-(benzylmercapto)-methyl para-bromophenylsulfone | alpha-(para-bromophenylsulfonyl)-alpha,alpha-dichloro-methane-sulfenyl chloride |
| 23 | alpha-(benzylmercapto)-methyl 3-chloro-4-bromphenylsulfone | alpha-(3-chloro-4-bromophenylsulfonyl)-alpha,alpha-dichloro-methane-sulfenyl chloride |
| 24 | alpha-(benzylmercapto)-methyl 3,4-dibromophenylsulfone | alpha-(3,4-dibromophenylsulfonyl)-alpha,alpha-dichloro-methane-sulfenyl chloride |
| 25 | alpha-(benzylmercapto)-methyl 3,4,5-trichlorophenylsulfone | alpha-(3,4,5-trichlorophenylsulfonyl)-alpha,alpha-dichloro-methane-sulfenyl chloride |
| 26 | alpha-(benzylmercapto)-methyl 3,5-dichloro-4-bromophenylsulfone | alpha-(3,5-dichloro-4-bromophenylsulfonyl)-alpha,alpha-dichloro-methane-sulfenyl chloride |
| 27 | alpha-(benzylmercapto)-methyl meta-methylphenylsulfone | alpha-(meta-methylphenylsulfonyl)-alpha,alpha-dichloro-methane-sulfenyl chloride |
| 28 | alpha-(benzylmercapto)-methyl para-methylphenylsulfone | alpha-(para-methylphenylsulfonyl)-alpha,alpha-dichloro-methane-sulfenyl chloride |
| 29 | alpha-(benzylmercapto)-methyl-3,4-dimethyl- | alpha-(3,4-dimethylphenylsulfonyl)-alpha,alpha- |

-continued

| EXAMPLE | COLUMN A | COLUMN B |
|---|---|---|
| 30 | phenylsulfone<br>alpha-(benzylmercapto)-methyl-3,5-dimethyl-<br>phenylsulfone | dichloro-methane-sulfenyl chloride<br>alpha-(3,5-dimethylphenylsulfonyl)-alpha,alpha-<br>dichloro-methane-sulfenyl chloride |
| 31 | alpha-(benzylmercapto)-methyl-para-ethyl-<br>phenylsulfone | alpha-(para-ethylphenylsulfonyl)-alpha,alpha<br>dichloro-methane-sulfenyl chloride |
| 32 | alpha-(benzylmercapto)-methyl-meta-chloro-<br>methylphenylsulfone | alpha-(meta-chloromethylphenylsulfonyl)-alpha,<br>alpha-dichloro-methane-sulfenyl chloride |
| 33 | alpha-(benzylmercapto)-methyl-3,4-diethyl-<br>phenylsulfone | alpha-(3,4-diethylphenylsulfonyl)-alpha,alpha-<br>dichloro-methane-sulfenyl chloride |
| 34 | alpha-(benzylmercapto)-methyl-3,4,5-tri-<br>methylphenylsulfone | alpha-(3,4,5-trimethylphenylsulfonyl)-alpha,alpha-<br>dichloro-methane-sulfenyl chloride |
| 35 | alpha-(benzylmercapto)-methyl-3,5-dichloro-<br>methylphenylsulfone | alpha-(3,5-dichloromethylphenylsulfonyl)-alpha,<br>alpha-dichloro-methane-sulfenyl chloride |
| 36 | alpha-(benzylmercapto)-methyl-3,4,5-tri-<br>bromophenylsulfone | alpha-(3,4,5-tribromophenylsulfonyl)-alpha,alpha-<br>dichloro-methane-sulfenyl chloride |

EXAMPLES 37 THROUGH 56

These examples illustrate the preparation by the method of this invention of alpha,alpha-dichloro-methane-sulfenyl chlorides of the formula E-CCl$_2$-S-Cl and intermediary alpha-chloromethylbenzyl sulfides of the formula

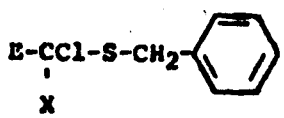

wherein X is hydrogen or chloro and E is

and A is aryl or halogenated aryl.

EXAMPLE 37

To a suitable reaction vessel equipped with a thermometer and agitator charged with an aqueous solution containing approximately 200 parts by weight of water and approximately 19 parts by weight of sodium hydroxide is added with agitation approximately 57.5 parts by weight of benzyl mercaptan. Thereafter a hot ethanol solution containing approximately 785 parts by weight of ethanol and approximately 108 parts by weight of alpha-bromo-para-chloroacetophenone is added with agitation. Thereupon the mass is heated to the reflux temperature and then refluxed for about 2 hours. The mass is then cooled and thereto is added with agitation approximately 1,000 parts by weight of cold water. Thereafter the precipitate is filtered off and identified as alpha-(benzylmercapto)-para-chloroacetophenone.

In a similar manner the following precursors of the manufacture of this invention are prepared: alpha-(benzylmercapto)-acetophenone, alpha-(benzylmercapto)-para-bromoacetophenone, alpha-(benzymercapto)-ortho-bromoacetophenone, alpha-(benzylmercapto)-para-fluoroacetophenone, alpha-(benzylmercapto)-meta-chloroacetophenone, and the like employing benzyl mercaptan and the appropriate substituted acetophenone, for example, alpha-chloroacetophenone, alpha-bromo-para-bromoacetophenone, alpha-bromo-ortho-bromoacetophenone, alpha-chloro-para-fluoroacetophenone, alpha-chloro-meta-chloroacetophenone, and the like, in the presence of a hydrogen halide scavenging agent. Likewise di-, tri- and higher halogenated precursors can be prepared by the above-described methods and used in the manufacture of substituted alpha-chloro-alpha-(chloromercapto)-acetophenones and intermediary products by the method of the present invention.

EXAMPLE 38

To a suitable reaction vessel equipped with a thermometer and agitator charged with an aqueous solution containing approximately 200 parts by weight of water and approximately 19 parts by weight of sodium hydroxide is added with agitation approximately 57.5 parts by weight of benzyl mercaptan. Thereafter a hot ethanol solution containing approximately 785 parts by weight of ethanol and approximately 100 parts by weight of alpha-bromo-paramethylacetophenone is added with agitation. Thereupon the mass is heated to the reflux temperature and then refluxed for about 2 hours. The mass is then cooled and thereto is added with agitation approximately 1,000 parts by weight of cold water. Thereafter the precipitate is filtered off and identified as alpha-(benzylmercapto)-para-methylacetophenone.

In a similar manner the following precursors of the manufacture of this invention are prepared: alpha-benzylmercaptomethyl naphthyl ketone, alpha-(benzylmercapto)-para-ethylacetophenone, alpha-(benzylmercapto)-ortho-methylacetophenone, alpha-(benzylmercapto)-para-propyl-acetophenone, alpha-(benzylmercapto)-meta-methylacetophenone, employing benzyl mercaptan and the appropriate aromatic ketone, for example, chloromethyl naphthyl ketone, alpha-bromo-para-ethylacetophenone, alpha-bromo-ortho-methylacetophenone, alpha-chloro-para-propylacetophenone, alpha-chloro-meta-methylacetophenone, and the like, in the presence of a hydrogen halide scavenging agent. Likewise, other benzylmercaptomethyl aryl ketone precursors can be prepared by the above-described methods and used in the manufacture of the alpha,alpha-dichloro-alpha-chloromercaptomethyl aryl ketones and intermediary products by the method of the present invention.

EXAMPLE 39

To a suitable reaction vessel equipped with a thermometer, agitator and venting means is charged approximately 25.6 parts by weight alpha-(benzylmercapto)-para-methylacetophenone dissolved in approximately 275 parts by weight of methylene chloride. While agitating the so-charged mass at about 0°C. is slowly added approximately 40 parts by weight of sulfuryl chloride. The reaction is exothermic and the temperature during the addition is permitted to rise to about 20°C. Upon completion of the sulfuryl chloride addition, the mass is agitated for about three hours at about room temperature. Thereafter the mass is stripped of volatiles under vacuum to give a liquid residue which residue is dissolved in petroleum ether solvent, crystallized by cooling the solution to about −70°C, separated from the solvent by filtration and identified as alpha,alpha-dichloro-alpha-(para-methylbenzoyl)-methane-sulfenyl chloride.

EXAMPLES 40 THROUGH 44

The procedure of Example 39 is followed except that in place of alpha-(benzylmercapto)-para-methylacetophenone in the amount of about 25.6 parts by weight a substituted alpha-(benzylmercapto)-acetophenone as shown in Column A is added in an amount such that the molecular proportion of benzylmercaptomethyl aryl ketone to sulfuryl chloride is 1 to 3. By this method, the corresponding dichloromercapto-methyl aryl ketone is prepared as shown in Column B.

| EXAMPLE NO. | A | B |
| --- | --- | --- |
| 40 | alpha-(benzylmercapto)-para-ethylacetophenone | alpha,alpha-dichloro-alpha-(para-ethylbenzoyl)-methane-sulfenyl chloride |
| 41 | alpha-(benzylmercapto)-ortho-methylacetophenone | alpha,alpha-dichloro-alpha-(ortho-methylbenzoyl)-methane-sulfenyl chloride |
| 42 | alpha-(benzylmercapto)-para-propylacetophenone | alpha,alpha-dichloro-alpha-(para-propylbenzoyl)-methane-sulfenyl chloride |
| 43 | alpha-(benzylmercapto)-meta-methylacetophenone | alpha,alpha-dichloro-alpha-(meta-methylbenzoyl)-methane-sulfenyl chloride |
| 44 | benzylmercapto-methyl-naphthyl ketone | alpha,alpha-dichloro-alpha-(chloromercapto)-methane-naphthyl ketone |

EXAMPLE 45

The procedure of Example 39 is followed except that the reaction is carried out under reflux and, instead of charging to the system 40 parts by weight of sulfuryl chloride, chlorine gas is bubbled through the refluxing mass until approximately 21 parts by weight thereof is absorbed. Alpha,alpha-dichloro-alpha-(para-methylbenzoyl)-methane-sulfenyl chloride is obtained. In this fashion, other alpha,alpha-dichloro-alpha-(chloromercapto)-methyl aryl ketones may likewise be prepared. Alpha,alpha-dichloro-alpha-(chloromercapto)-methyl aryl ketones are useful as preemergent herbicides.

EXAMPLE 46

To a suitable reaction vessel equipped with a thermometer, agitator and venting means is charged approximately 13.8 parts by weight alpha-(benzylmercapto)-para-chloroacetophenone dissolved in approximately 275 parts by weight of methylene chloride. While agitating the so-charged mass at about 0°C is slowly added approximately 21 parts by weight of sulfuryl chloride. The reaction is exothermic and the temperature during the addition is permitted to rise to about 20°C. Upon completion of the sulfuryl chloride addition, the mass is agitated for about 3 hours at about room temperature. Thereafter the mass is stripped of volatiles under vacuum to give a liquid residue which residue is dissolved in petroleum ether solvent, crystallized by cooling the solution to about −70°C, separated from the solvent by filtration and identified as alpha,alpha-dichloro-alpha-(para-chlorobenzoyl)-methane-sulfenyl chloride.

Alpha,alpha-dichloro-alpha-(para-chlorobenzoyl)-methanesulfenyl chloride exhibited preemergent herbicidal activity to cocklebur, Canada thistle, velvet leaf and smartweed.

EXAMPLES 47 THROUGH 51

The procedure of Example 46 is followed except that in place of alpha-(benzylmercapto)-4-chloroacetophenone in the amount of about 13.8 parts by weight a substituted alpha-(benzylmercapto)-acetophenone as shown in column A is added in an amount such that the molecular proportion of alpha-(benzylmercapto)-acetophenone to sulfuryl chloride is 1 to 3. By this method, the corresponding alpha-chloro-alpha-(chlorothio)-acetophenone is prepared as shown in column B.

| EXAMPLE NO. | A | B |
| --- | --- | --- |
| 47 | alpha-(benzylmercapto)-para-bromoacetophenone | alpha,alpha-dichloro-alpha-(para-bromobenzoyl)-methane-sulfenyl chloride |
| 48 | alpha-(benzylmercapto)-ortho-bromoacetophenone | alpha,alpha-dichloro-alpha-(ortho-bromobenzoyl)-methane-sulfenyl chloride |
| 49 | alpha-(benzylmercapto)-para-fluoroacetophenone | alpha,alpha-dichloro-alpha-(para-fluorobenzoyl)-methane-sulfenyl chloride |
| 50 | alpha-(benzylmercapto)-meta-chloroacetophenone | alpha,alpha-dichloro-alpha-(meta-chlorobenzoyl)-methane-sulfenyl chloride |
| 51 | alpha-(benzylmercapto)-acetophenone | alpha,alpha-dichloro-alpha-benzoyl-methane-sulfenyl chloride |

EXAMPLE 52

To a suitable reaction vessel equipped with a thermometer, agitator and venting means is charged approximately 25.6 parts by weight of alpha-(benzylmercapto)-para-methylacetophenone dissolved in approximately 300 parts by weight of 1,2-dichloroethane. While agitating the so-charged mass at about 0°C. is slowly added approximately 26 parts by weight of sulfuryl chloride. The reaction is exothermic and the temperature during the addition is permitted to rise to about 20°C. Upon completion of the sulfuryl chloride addition, the mass is agitated for about 1 hour at about room temperature. Thereafter, the mass is stripped of volatiles under vacuum to give a liquid residue which residue is dissolved in petroleum ether solvent, crystallized by cooling the solution to about −70°C, separated from the solvent by filtration and identified as alpha,alpha-dichloro-alpha-(benzylmercapto)-para-methylacetophenone.

In similar fashion, other chloro-benzylmercaptomethyl aryl ketones can be prepared from the corresponding benzylmercaptomethyl aryl ketones.

EXAMPLE 53

The procedure of Example 52 is followed except that in place of 25.6 parts by weight of alpha-(benzylmercapto)-paramethylacetophenone an equimolecular proportion of alpha-(benzylmercapto)-acetophenone is used. The product obtained is alpha,alpha-dichloro-alpha-(benzylmercapto)-acetophenone.

In similar fashion, substituted alpha-chloro-alpha-(benzylmercapto)-acetophenones can be prepared from the corresponding substituted alpha-(benzylmercapto)-acetophenones.

EXAMPLE 54

The procedure of Example 53 is followed except that the reaction is carried out under reflux and instead of charging to the system 26 parts by weight of sulfuryl chloride, chlorine gas is bubbled through the refluxing mass until approximately 14 parts by weight thereof is absorbed. Alpha,alpha-dichloro-alpha-(benzylmercapto)-acetophenone is obtained.

In similar fashion, substituted alpha-chloro-alpha-(benzylmercapto)-acetophenones can be prepared from the corresponding substituted alpha-(benzylmercapto)-acetophenones.

EXAMPLE 55

The procedure of Example 52 is followed except that the reaction is carried out under reflux and, instead of charging to the system 26 parts by weight of sulfuryl chloride, chlorine gas is bubbled through the refluxing mass until approximately 14 parts by weight thereof is absorbed. Alpha,alpha-dichloro-alpha-(benzylmercapto)-para-methylacetophenone is obtained.

In similar fashion, other chloro-benzylmercapto methyl aryl ketones can be prepared from the corresponding substituted benzylmercapto methyl aryl ketones.

EXAMPLE 56

The procedure of Example 46 is followed except that the reaction is carried out under reflux and, instead of charging to the system 21 parts by weight of sulfuryl chloride, chlorine gas is bubbled through the refluxing mass until approximately 11 parts by weight thereof is absorbed. Alpha,alpha-dichloro-alpha-(para-chlorobenzoyl)-methane-sulfenyl chloride is obtained. In this fashion, other alpha-chloro-alpha-(chloromercapto)acetophenones may likewise be prepared.

EXAMPLES 57 THROUGH 68

These examples illustrate the preparation by the method of this invention of alpha,alpha-dichloromethanesulfenyl chlorides of the formula $E-CCl_2-S-Cl$ and intermediary alpha-chloromethylbenzyl sulfides of the formula

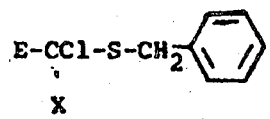

wherein X is hydrogen or chloro and E is

and B is alkyl, trihalogenated methyl, or $-CH_2Y$ wherein Y is alkyl having at least three carbon atoms, halogenated alkyl or halogenated phenyl with from one through three halogen substituents.

EXAMPLE 57

To a suitable reaction vessel equipped with a thermometer and agitator charged with an aqueous solution containing approximately 200 parts by weight of water and approximately 20 parts by weight of sodium hydroxide is added with agitation approximately 62 parts by weight of benzyl mercaptan. Thereafter approximately 114 parts by weight of benzyl alpha-bromoacetate is added with agitation. Thereupon the mass is agitated at room temperature for about 1 hour. Thereafter the mass is extracted with methylene chloride. The methylene chloride is distilled off leaving a liquid identified as benzyl alpha-(benzylmercapto)-acetate.

EXAMPLE 58

To a suitable reaction vessel equipped with a thermometer and agitator charged with an aqueous solution containing approximately 200 parts by weight of water and approximately 20 parts by weight of sodium hydroxide is added with agitation approximately 83 parts by weight of methyl bromoacetate. Thereafter approximately 67 parts by weight of benzyl mercaptan is added with agitation. Thereupon the mass is agitated at room temperature for about 1 hour. Thereafter the mass is extracted with methylene chloride. The methylene chloride is distilled off leaving a liquid identified as methyl alpha-(benzylmercapto)-acetate.

Similarly propyl alpha-(benzylmercapto)-acetate, isopropyl alpha-(benzylmercapto)-acetate, ethyl alpha-(benzylmercapto)-acetate, butyl alpha-(benzylmercapto)-acetate, isobutyl alpha-(benzylmercapto)-acetate, trichloromethyl alpha-(benzylmercapto)-acetate and the like may be prepared from propyl alpha-bromoacetate, isopropyl bromoacetate, ethyl alpha-bromoacetate, butyl alpha-bromoacetate, isobutyl alpha-bromoacetate, trichloromethyl alpha-bromoacetate and benzyl mercaptan respectively.

EXAMPLE 59

To a suitable reaction vessel equipped with a thermometer, agitator and venting means is charged approximately 27.2 parts by weight of benzyl alpha-(benzylmercapto)-acetate dissolved in approximately 275 parts by weight of methylene chloride. While agitating the so-charged mass at about 0°C. is slowly added approximately 40 parts by weight of sulfuryl chloride. The reaction is exothermic and the temperature during the addition is permitted to rise to about 20°C. Upon completion of the sulfuryl chloride addition the mass is agitated for about 2 hours at about room temperature. Thereafter the mass is stripped of volatiles under vacuum to give a liquid residue [composed chiefly of an equimolar mixture of benzyl alpha-(chloromercapto)-alpha,alpha-dichloroacetate and by-product benzyl chloride] which residue is fractionally distilled and the yellow liquid is identified as benzyl alpha(chloromercapto)-alpha,alpha-dichloroacetate.

EXAMPLE 60

To a suitable reaction vessel equipped with a thermometer, agitator and reflux condenser is charged approximately 21.0 parts by weight of benzyl alpha-(benzylmercapto)-acetate dissolved in approximately 300 parts by weight of chloroform. The so-charged mass is heated to reflux and, while refluxing, gaseous chlorine is sparged into the refluxing mass until approximately 17 parts by weight thereof is absorbed. The mass is then stripped of volatiles to give a liquid residue, which upon fractionally distilling yields a yellow liquid identified as benzyl alpha-(chloromercapto)-alpha, alpha-dichloroacetate.

EXAMPLE 61

To a suitable reaction vessel equipped with a thermometer, agitator and venting means is charged approximately 21.0 parts by weight of benzyl alpha-(benzylmercapto)-acetate in approximately 250 parts by weight of 1,2-dichloroethane. While maintaining the so-charged mass at about 0°C. there is added with agitation approximately 11 parts by weight of sulfuryl chloride. Upon completion of the sulfuryl chloride addition the volatiles are distilled off and gaseous chlorine bubbled through the mass at about 70°C. until approximately 11 parts thereof is absorbed. The mass is then stripped of volatiles to give a liquid residue, which upon fractionally distilling yields a yellow liquid identified as benzyl alpha-(chloromercapto)-alpha,alpha-dichloroacetate.

EXAMPLE 62

To a suitable reaction vessel equipped with a thermometer, agitator and venting means is charged approximately 19.6 parts by weight of methyl alpha-(benzylmercapto)-acetate dissolved in approximately 275 parts by weight of methylene chloride. While agitating the so-charged mass at about 0°C. is slowly added approximately 50 parts by weight of sulfuryl chloride. The reaction is exothermic and the temperature during the addition is permitted to rise to about 20°C. Upon completion of the sulfuryl chloride addition the mass is agitated for about 1 hour at about room temperature. Thereafter the mass is stripped of volatiles under vacuum to give a liquid residue [composed chiefly of an equimolar mixture of methyl alpha-(chloromercapto)-alpha,alpha-dichloroacetate and by-product benzyl chloride] which residue is fractionally distilled and the yellow liquid is identified as methyl alpha-(chloromercapto)-alpha,alpha-dichloroacetate.

Similarly propyl alpha-(chloromercapto)-alpha,alpha-dichloroacetate, isopropyl alpha-(chloromercapto)-alpha,alpha-dichloroacetate, ethyl alpha-(chloromercapto)-alpha,alpha-dichloroacetate, butyl alpha-(chloromercapto)-alpha,alpha-dichloroacetate, isobutyl alpha-(chloromercapto)-alpha,alpha-dichloroacetate, trichloromethyl alpha-(chloromercapto)-alpha,alpha-dichloroacetate and the like may be prepared from propyl alpha-(benzylmercapto)-acetate, isopropyl alpha-(benzylmercapto)-acetate, ethyl alpha-(benzylmercapto)-acetate, butyl alpha-(benzylmercapto)-acetate, isobutyl alpha-(benzylmercapto)-acetate, trichloromethyl alpha-(benzylmercapto)-acetate and the corresponding alpha-(benzylmercapto)-acetates.

EXAMPLE 63

The procedure of Example 62 is followed except that the reaction is carried out under reflux and, instead of charging to the system 50 parts by weight of sulfuryl chloride, chlorine gas is bubbled through the refluxing mass until approximately 26 parts by weight thereof is absorbed. Methyl alpha-(chlorothio)-alpha, alpha-dichloroacetate is obtained. Similarly, other alkyl alpha-(chloromercapto)-alpha,alpha-dichloroacetates can be prepared. Alkyl alpha-(chloromercapto)-alpha,alpha-dichloroacetates are useful as pre-emergent herbicides.

EXAMPLE 64

This example is illustrative of the preparation of alkyl alpha-(benzylmercapto)-alpha,alpha-dichloroacetates but not limitative thereof.

To a suitable reaction vessel equipped with a thermometer, agitator and venting means is charged approximately 85.0 parts by weight of methyl alpha-(benzylmercapto)-acetate dissolved in approximately 275 parts by weight of methylene chloride. While agitating the so-charged mass at about 0°C. is slowly added approximately 115 parts by weight of sulfuryl chloride. The reaction is exothermic and the temperature during the addition is permitted to rise to about 20°C. Upon completion of the sulfuryl chloride addition the mass is agitated for about 1 hour at about room temperature. Thereafter the mass is stripped of volatiles under vacuum to give a liquid residue. The residue then is fractionally distilled and the yellow liquid is identified as methyl alpha-(benzylmercapto)-alpha,alpha-dichloroacetate. Similarly, other alkyl alpha-(benzylmercapto)-alpha-chloroacetates can be prepared.

EXAMPLE 65

To a suitable reaction vessel equipped with a thermometer, agitator and venting means is charged approximately 21.0 parts by weight of ethyl alpha-(benzylmercapto)-acetate dissolved in approximately 275 parts by weight of methylene chloride. While agitating the so-charged mass at about 0°C. is slowly added approximately 40.2 parts by weight of sulfuryl chloride. The reaction is exothermic and the temperature during the addition is permitted to rise to about 20°C. Upon completion of the sulfuryl chloride addition the mass is agitated for about 2 hours at about room temperature. Thereafter the mass is stripped of volatiles under vacuum to give a liquid residue [composed chiefly of an equimolar mixture of ethyl alpha-(chloromercapto)-alpha,alpha-dichloroacetate and by-product benzyl chloride] which residue is fractionally distilled and the yellow liquid collected at 81°-82°C at 10 mm. of mercury is identified as ethyl alpha(chloromercapto)-alpha,alpha-dichloroacetate.

EXAMPLE 66

To a suitable reaction vessel equipped with a thermometer, agitator and reflux condenser is charged approximately 21.0 parts by weight of ethyl alpha-(benzylmercapto)-acetate dissolved in approximately 300 parts by weight of chloroform. The so-charged mass is heated to reflux and while refluxing gaseous chlorine is sparged into the refluxing mass until approximately 21.3 parts by weight thereof is absorbed. The mass is then stripped of volatiles to give a liquid residue, which upon fractionally distilling yields a yellow liquid identified as ethyl alpha-(chloromercapto)-alpha,alpha-dichloroacetate (b.p. 81°-82°C. at 10 mm. of mercury).

EXAMPLE 67

To a suitable reaction vessel equipped with a thermometer, agitator and venting means is charged approximately 21.0 parts by weight of ethyl alpha-(benzylmercapto)-acetate in approximately 250 parts by weight of 1,2-dichloroethane. While maintaining the so-charged mass at about 0°C. there is added with agitation approximately 27 parts by weight of sulfuryl chloride. Upon completion of the sulfuryl chloride addition the volatiles are distilled off and gaseous chlorine bubbled through the mass at about 70°C. until approximately 7.1 parts thereof is absorbed. Thereafter the mass is stripped of volatiles under vacuum to give a liquid residue which residue is fractionally distilled and the yellow liquid is identified as ethyl alpha-(chloromercapto)-alpha,alpha dichloroacetate.

EXAMPLE 68

This example illustrates the preparation of ethyl alpha-(chloromercapto)-alpha,alpha-dichloroacetate from ethyl alpha-(benzylmercapto)-acetate and chlorine.

The procedure of Example 1 is followed except that the reaction is carried out under reflux and, instead of charging to the system 40.2 parts by weight of sulfuryl chloride, chlorine gas is bubbled through the refluxing mass until approximately 21.3 parts by weight thereof is absorbed. Ethyl alpha-(chloromercapto)-alpha,alpha-dichloroacetate is obtained.

Ethyl alpha-(chloromercapto)-alpha,alpha-dichloroacetate exhibited preemergent herbicidal activity against velvet leaf and morning glory.

EXAMPLES 69 THROUGH 72

These examples illustrate the preparation by the method of this invention of alpha,alpha-dichloromethane-sulfenyl chlorides of the formula E-CCl$_2$-S-Cl and intermediary alpha-chloromethylbenzyl sulfides of the formula

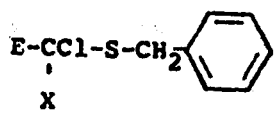

wherein X is hydrogen or chloro and E is

EXAMPLE 69

To a suitable reaction vessel equipped with a thermometer and agitator charged with an aqueous solution containing approximately 200 parts by weight of water and approximately 20 parts by weight of sodium hydroxide is added with agitation approximately 62 parts by weight of benzyl mercaptan. Thereafter approximately 62 parts by weight of alpha-bromoacetaldehyde is added with agitation. Thereupon the mass is agitated at room temperature for about 1 hour. Thereafter the water is distilled off leaving a liquid identified as alpha-(benzylmercapto)-acetaldehyde.

EXAMPLE 70

To a suitable reaction vessel equipped with a thermometer, agitator and venting means is charged approximately 16.6 parts by weight of alpha-(benzylmercapto)-acetaldehyde dissolved in approximately 275 parts by weight of methylene chloride. While agitating the so-charged mass at about 0°C. is slowly added approximately 40 parts by weight of sulfuryl chloride. The reaction is exothermic and the temperature during the addition is permitted to rise to about 20°C. Upon completion of the sulfuryl chloride addition the mass is agitated for about 2 hours at about room temperature. Thereafter the mass is stripped of volatiles under vacuum to give a liquid residue [composed chiefly of an equimolar mixture of alpha(chloromercapto)-alpha,alpha-dichloroacetaldehyde and by-product benzyl chloride] which residue is fractionally distilled and the yellow liquid is identified as alpha-(chloromercapto)-alpha,alpha-dichloroacetaldehyde

EXAMPLE 71

To a suitable reaction vessel equipped with a thermometer, agitator and reflux condenser is charged approximately 16.6 parts by weight of alpha-(benzylmercapto)-acetaldehyde dissolved in approximately 300 parts by weight of chloroform. The so-charged mass is heated to reflux and while refluxing gaseous chlorine is sparged into the refluxing mass until approximately 21 parts by weight thereof is absorbed. The mass is then stripped of volatiles to give a liquid residue, which upon fractionally distilling yields a yellow liquid identified as alpha-(chloromercapto)-alpha,alpha-dichloro-acetaldehyde. Alpha-(chloromercapto)-alpha,alpha-dichloro-acetaldehyde exhibited insecticidal activity against southern corn rootworm.

EXAMPLE 72

This example is illustrative of the preparation of alpha-(benzylmercapto)-alpha,alpha-dichloroacetaldehyde but not limitative thereof.

To a suitable reaction vessel equipped with a thermometer, agitator and venting means is charged approximately 83 parts by weight of alpha-(benzylmercapto)-acetaldehyde dissolved in approximately 275 parts by weight of methylene chloride. While agitating the so-charged mass at about 0°C. is slowly added approximately 134 parts by weight of sulfuryl chloride.

The reaction is exothermic and the temperature during the addition is permitted to rise to about 20°C. Upon completion of the sulfuryl chloride addition the mass is agitated for about 1 hour at about room temperature. Thereafter the mass is stripped of volatiles under vacuum to give a liquid residue. The residue then is fractionally distilled and the yellow liquid is identified as alpha-(benzylmercapto)-alpha,alpha-dichloroacetaldehyde.

EXAMPLE 73

The procedure for testing pre-emergent herbicidal activity of representative substituted alpha,alpha-dichloro-methanesulfenyl chlorides of this invention and their intermediaries is as follows:

A good grade of top soil is placed in aluminum pans and compacted to a depth of ⅜ to ½ inch from the top of the pan. A pre-determined number seeds of each of several plant species are placed on top of the soil in the pans. The seeds are covered with soil and the pan leveled. The herbicidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

EXAMPLE 74

The procedure for testing insecticidal activity of representative substituted alpha,alpha-dichloro-methane sulfenyl chlorides of this invention and their intermediaries against the southern corn rootworm is as follows:

To a growth pouch (diSPo Seed-Pak growth pouch, Catalog No. B1220, of Scientific Products Division of American Hospital Supply Corporation, Evanston, Illinois) in an upright position is added 20 ml. of distilled water. Thereafter is added 0.1 ml. of an acetone solution of known concentration in percent by weight of a compound of this invention (for example a 0.1 ml. of a 0.1% by weight acetone solution of the compound provides a concentration of 5.0 ppm thereof). In the trough of the pouch formed by the paper wick thereof are placed two corn seeds (*Zea mays*, Hybrid U.S. 13) about one inch apart. Thereupon to the trough and between the seeds is added 8 to 12 ready-to-hatch eggs of the southern corn rootworm (*Diabrotica undecimpunctata howardi*) which eggs are washed (with distilled water) free of the soil in which they are incubated at room temperature for 21 days immediately prior to their placement in the trough. The so-charged growth pouch is then placed in an upright position in an incubator maintained at 80°F. and 70% relative humidity for 14 days. Immediately thereafter the growth pouches are removed and the extent of kill of the corn rootworm larvae is observed.

While this invention has been described with respect to certain embodiments it is to be understood that it is not so limited and that variations and modifications thereof obvious to those skilled in the art to which this invention appertains can be made without departing from the spirit or scope thereof.

The embodiments of the invention in which an exclusive property or privilege is claimed is as follows:

1. A substituted alpha-chloro-benzyl sulfide of the formula

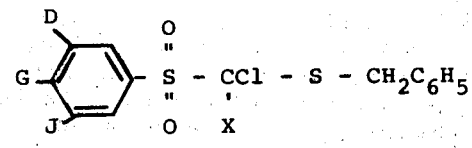

wherein X is hydrogen or chloro and D, G and J are hydrogen, bromo, chloro or alkyl.

2. A compound of claim 1 wherein J, G and D respectively are hydrogen.

3. A compound of claim 1 wherein J and D are hydrogen and wherein G is chloro.

4. A compound of claim 1 wherein G and D are chloro and wherein J is hydrogen.

* * * * *

UNITED STATES PATENT OFFICE
CERTIFICATE OF CORRECTION

PATENT NO. : 3,988,375
DATED : October 26, 1976
INVENTOR(S) : Wendell Gary Phillips It is certified that error appears in the above-identified patent and that said Letters Patent are hereby corrected as shown below:

Column 3, lines 5 and 6, the chemical name "alpha-phenyl-sulfonyl-alpha,alpha-dichloro-methane-sulfenyl" should read -- alpha-(phenylsulfonyl)-alpha,alpha-dichloro-methane-sulfenyl chloride, --.

Column 23, Example 73, line 19, after "number" the word -- of -- has been left out.

Signed and Sealed this

Tenth Day of May 1977

[SEAL]

Attest:

RUTH C. MASON
*Attesting Officer*

C. MARSHALL DANN
*Commissioner of Patents and Trademarks*